United States Patent [19]
Ismael

[11] Patent Number: 5,891,111
[45] Date of Patent: Apr. 6, 1999

[54] FLEXIBLE SURGICAL DRAIN WITH A PLURALITY OF INDIVIDUAL DUCTS

[75] Inventor: Bernard Ismael, Paris, France

[73] Assignee: Porgés, LePlessis Robinson, France

[21] Appl. No.: 50,102

[22] Filed: Mar. 30, 1998

[30] Foreign Application Priority Data

Apr. 14, 1997 [FR] France ................................. 97 04532

[51] Int. Cl.$^6$ .............................. A61M 25/00; F16L 9/18
[52] U.S. Cl. ........................ 604/280; 604/264; 604/284; 138/116
[58] Field of Search ..................... 604/264, 280, 604/43, 93, 284; 138/111, 112, 113, 115, 116, 117, 118

[56] References Cited

U.S. PATENT DOCUMENTS

| | | | |
|---|---|---|---|
| 4,406,656 | 9/1983 | Hattler et al. ........................... | 604/280 |
| 4,717,379 | 1/1988 | Ekholmer ................................. | 604/43 |
| 4,925,452 | 5/1990 | Melinyshyn et al. ................... | 604/284 |
| 5,100,395 | 3/1992 | Rosenberg .............................. | 604/284 |
| 5,800,414 | 9/1998 | Cazal ...................................... | 604/280 |

FOREIGN PATENT DOCUMENTS

| | | |
|---|---|---|
| 0332366 | 9/1989 | European Pat. Off. . |
| 0385168 | 9/1990 | European Pat. Off. . |
| 0386408 | 9/1990 | European Pat. Off. . |
| 2820239 | 11/1978 | Germany . |
| 8815869 | 3/1989 | Germany . |

*Primary Examiner*—Wynn Wood Coggins
*Assistant Examiner*—LoAn H. Thanh
*Attorney, Agent, or Firm*—Fisher, Christen & Sabol

[57] ABSTRACT

The invention relates to a surgical drain (1) comprising a plurality of individual ducts (2–7) juxtaposed and joined in pairs.

According to the invention this drain is in the form of a tube whose wall is composed of said individual juxtaposed ducts (2–7).

4 Claims, 1 Drawing Sheet

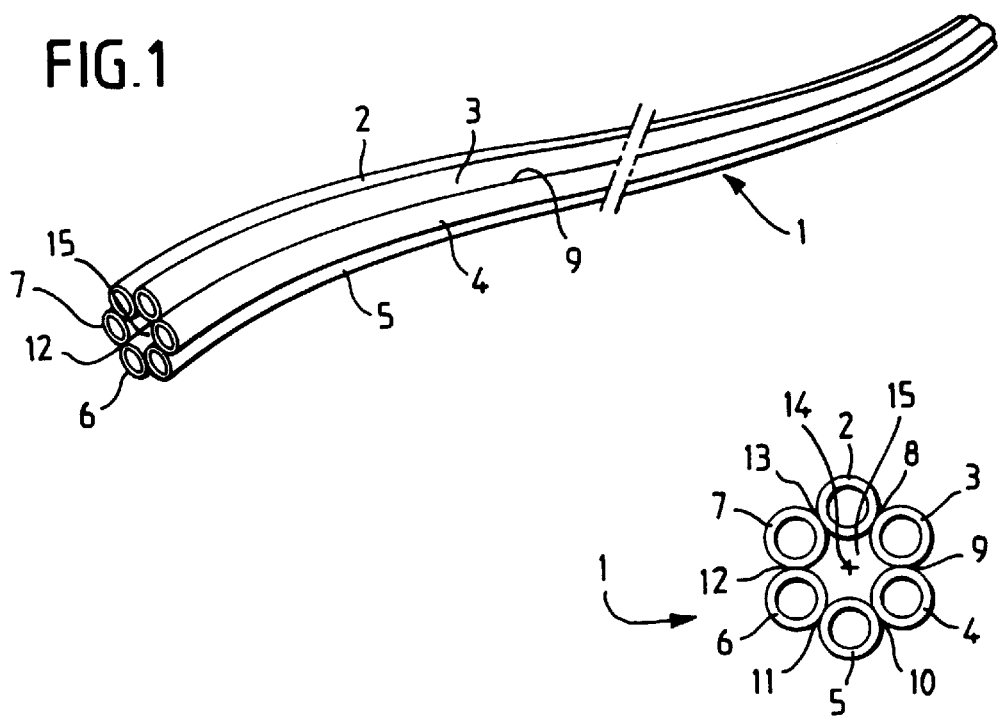
FIG.1
FIG.2
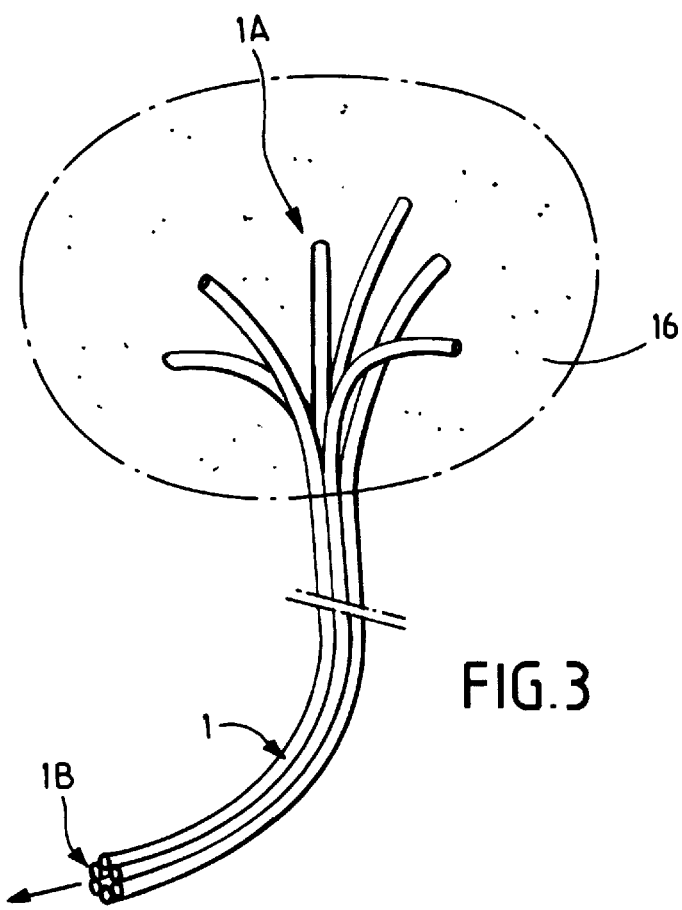
FIG.3

FLEXIBLE SURGICAL DRAIN WITH A PLURALITY OF INDIVIDUAL DUCTS

FIELD OF THE INVENTION

This invention relates to flexible surgical drains with several individual ducts for draining biological cavities such as wounds, abscesses and so forth.

PRIOR ART

The prior art already includes surgical drains of this kind in which a plurality of individual parallel ducts are juxtaposed and joined in twos in such a way as to form a flat strip made up of a single layer of ducts, its thickness being determined only by the diameter of said ducts and its width by the number and diameter of said ducts. Thus, if the number of individual ducts is large (for example of the order of 5 to 10), the width of such a drain is large.

Such a multiple-duct drain in the form of a flat strip can be positioned in the cavity to be drained by introducing its distal end into the cavity. It will be observed that because said drain is so wide, the surgeon is obliged to make a large incision to give access or enlarge the access to said cavity. However, the individual ducts are usually separated from each other at the distal end of said drain so that they can be distributed widely around said cavity and therefore improve drainage. When this is done, the simple positioning method mentioned above cannot be used. The method must then be to introduce the drain into said cavity by its proximal end, having first made the abovementioned incision, and then to pass said proximal end back out of the patient through another incision and finally to pull this proximal end until the separated ducts at the distal end of the drain are in said cavity. The surgeon has therefore made two large incisions.

As a result, these known multiple-duct drains in the form of flat strips present the disadvantage of requiring one or two large incisions to be made. Additionally, given their width, not only is their withdrawal after draining the cavity often traumatizing for the patient, but also they cannot be used in laparoscopic surgery. Also, it is difficult, if not impossible, to connect their proximal end to an external device, for example to inject a washing fluid into the cavity and/or to aspirate fluids out of the cavity through an individual duct.

In an effort to find a remedy to these disadvantages, some surgeons have proposed rolling the drain on itself about its longitudinal axis to make it into a spiral-sectioned cylinder which can then be inserted and/or removed through a smaller incision, or, in laparoscopy, through a path left by a trocar. However, although such a method avoids some of the disadvantages cited above, it does not eliminate all of them: for example, connection to a washing or aspiration device is still impossible. In addition, it has its own disadvantages, such as the stagnation of biological fluids between the turns of the cylinder or the natural tendency for it to unroll or expand radially, making it difficult to remove the said drain.

SUMMARY OF THE INVENTION

The object of the present invention is to solve all the disadvantages of the known flat drains discussed above.

To this end, according to the invention, the surgical drain comprising a plurality of individual ducts juxtaposed and joined in twos is noteworthy in that it is in the form of a tube whose wall is composed of said individual juxtaposed ducts. Said individual juxtaposed ducts preferably define a central longitudinal passage between themselves. The section of such a central longitudinal passage may be of any desired shape, e.g. circular or hexagonal as mentioned below. It can of course be used in the same way as any of the individual ducts.

Thus, as with the flat drain rolled longitudinally upon itself, large incisions are avoided. In addition, however, in the drain according to the present invention:

the external diameter of the drain is constant, which facilitates its insertion through the inside of a trocar;

the central longitudinal passage is of constant section and biological fluids cannot be trapped; and the tubular shape makes it easy to produce connectors for connecting the proximal end to an external device, for example to perform aspirated drainage, with or without washing.

Clearly, owing to its tubular shape, the drain according to the invention can be used in conventional surgery as well as in laparoscopic surgery.

It will be observed that said individual juxtaposed ducts could run helically around the axis of the drain. However, in a preferred embodiment said individual juxtaposed ducts are straight and therefore parallel with each other and with the longitudinal axis of said drain.

Likewise said individual juxtaposed ducts could be dissimilar to each other, for example as regards their diameter. It is nevertheless advantageous for them all to be identical.

In order that said individual juxtaposed ducts can be separated from each other at the distal end of said drain, longitudinally tearable lines are provided between them.

In a preferred embodiment, the drain of the invention comprises six identical individual juxtaposed ducts defining a central longitudinal passage between themselves, the cross section of which is a regular hexagon with concave curved sides.

BRIEF DESCRIPTION OF THE DRAWINGS

The figures of the attached drawing will clearly explain how the invention can be carried out. In the figures, identical references denote similar parts.

FIG. 1 is a perspective view of the preferred embodiment of the tubular drain according to the present invention.

FIG. 2 shows the cross section of the tubular drain of FIG. 1.

FIG. 3 schematically illustrates the tubular drain of FIGS. 1–2 in the position of draining a biological cavity.

DESCRIPTION OF THE PREFERRED EMBODIMENT

The drain 1 in accordance with the present invention, shown in FIGS. 1 and 2, is composed of a plurality of identical individual straight ducts 2–7 joined in twos along straight longitudinal lines 8–13. In each section of said drain 1, the individual ducts 2–7 are distributed regularly around the center 14 of said section, so that said drain 1 is in the form of a tube whose wall is composed of said individual juxtaposed ducts which define between themselves, along the entire length of said drain 1, an internal longitudinal passage 15 of constant cross section in the form of a regular hexagon with concave curved sides.

The drain 1 according to the present invention is advantageously produced by extrusion of a biocompatible flexible synthetic material such as, for example, a silicone.

The longitudinal join lines 8–13 between the individual ducts 2–7 are advantageously tearable, so that in order to drain a biological cavity 16 more efficiently (see FIG. 3), said individual ducts 2–7 can be separated from each other at the distal end 1A of said drain 1 in said biological cavity 16 (a wound, abscess or the like). Said individual ducts 2–7 can thus be distributed around said cavity 16 and can drain different areas of it in parallel.

Although FIGS. 1–3 show a preferred embodiment with six identical straight individual ducts 2–7, it is self-evident that the drain in accordance with the present invention could have a different number of individual, not necessarily similar ducts.

It will be observed that, because of the tubular form of the drain 1, it is easy to form an endpiece (not shown) that can be fitted to the proximal end 1B of said drain in order to connect up the individual ducts to devices for injecting washing fluid or for aspiration, or even to a colostomy bag.

I claim:

1. A surgical drain having a longitudinal length and comprising at least five individual juxtaposed ducts that are tearable along said longitudinal length, said individual ducts being arranged as a tube envelope around said longitudinal length and defining a central longitudinal passage, the cross-section of which is a polygon with concave curved sides.

2. The drain as claimed in claim 1, in which said individual juxtaposed ducts are straight.

3. The drain as claimed in claim 1, in which said individual juxtaposed ducts are identical.

4. The drain as claimed in claim 1, compromising six individual juxtaposed ducts, the cross section of said central longitudinal passage being a regular hexagon with concave curved sides.

\* \* \* \* \*